United States Patent
Ash et al.

(10) Patent No.: US 7,713,226 B2
(45) Date of Patent: May 11, 2010

(54) ON DEMAND AND POST-TREATMENT DELIVERY OF SALINE TO A DIALYSIS PATIENT

(75) Inventors: Stephen R. Ash, Lafayette, IN (US); David J. Carr, West Lafayette, IN (US)

(73) Assignee: Renal Solutions, Inc., Warrendale, PA (US)

( * ) Notice: Subject to any disclaimer, the term of this patent is extended or adjusted under 35 U.S.C. 154(b) by 528 days.

(21) Appl. No.: 11/443,710

(22) Filed: May 31, 2006

(65) Prior Publication Data

US 2007/0161941 A1    Jul. 12, 2007

Related U.S. Application Data

(60) Provisional application No. 60/756,772, filed on Jan. 6, 2006.

(51) Int. Cl.
*A61M 37/00*   (2006.01)
*B01D 21/30*   (2006.01)
*C02F 1/44*    (2006.01)
*A61M 1/00*    (2006.01)

(52) U.S. Cl. .................. 604/4.01; 604/5.01; 604/6.01; 210/134; 210/139; 210/143; 210/646; 422/48

(58) Field of Classification Search ............... 604/4.01, 604/5.01, 6.06; 210/134, 138, 139, 143, 210/257.2, 646, 195.2; 422/48
See application file for complete search history.

(56) References Cited

U.S. PATENT DOCUMENTS

| | | | |
|---|---|---|---|
| 3,946,731 A | 3/1976 | Lichtenstein | |
| 4,204,957 A | 5/1980 | Weickhardt | |
| 4,661,246 A * | 4/1987 | Ash | 210/87 |
| 4,710,164 A | 12/1987 | Levin et al. | |
| 4,718,891 A | 1/1988 | Lipps | |
| 4,923,598 A | 5/1990 | Schal | |
| 4,995,268 A * | 2/1991 | Ash et al. | 73/861.05 |
| 5,178,763 A | 1/1993 | Delaunay | |
| 5,211,849 A | 5/1993 | Kitaevich et al. | |
| 5,247,434 A * | 9/1993 | Peterson et al. | 700/83 |
| 5,277,820 A * | 1/1994 | Ash | 210/646 |
| 5,314,825 A * | 5/1994 | Weyrauch et al. | 436/43 |
| 5,344,568 A | 9/1994 | Kitaevich et al. | |

(Continued)

OTHER PUBLICATIONS

International Search Report for corresponding PCT Application (PCT/US06/49548), 2 pages, Dated Sep. 25, 2007.

*Primary Examiner*—Leslie Deak
*Assistant Examiner*—Adam Marcetich
(74) *Attorney, Agent, or Firm*—Fish & Richardson P.C.

(57) ABSTRACT

Apparatus for use in a dialysis system are disclosed including an apparatus for delivering saline during dialysis treatment, an apparatus for delivering saline to a patient after dialysis treatment has ended, and an apparatus for alerting a patient that dialysis treatment is about to end. In the apparatus for delivering saline during dialysis treatment, a controller is configured to automatically deliver saline in response to a request. In the apparatus for delivering saline to a patient after dialysis treatment has ended, a controller is configured to automatically deliver saline after dialysis treatment has concluded, but before the patient is disconnected in response to a request. In the apparatus for alerting a patient that dialysis treatment is about to end, a controller is configured to monitor a dialysis treatment and activate an alarm when treatment is about to end.

4 Claims, 1 Drawing Sheet

U.S. PATENT DOCUMENTS

| | | | |
|---|---|---|---|
| 5,346,472 A | 9/1994 | Keshavaih et al. | |
| 5,366,630 A | 11/1994 | Chevallet | |
| 5,470,483 A | 11/1995 | Bene et al. | |
| 5,529,685 A * | 6/1996 | Irie et al. | 210/134 |
| 5,536,412 A | 7/1996 | Ash | |
| 5,609,770 A * | 3/1997 | Zimmerman et al. | 210/739 |
| 5,679,245 A | 10/1997 | Manica | |
| 5,690,831 A * | 11/1997 | Kenley et al. | 210/646 |
| 5,762,805 A | 6/1998 | Truitt et al. | |
| 5,776,345 A | 7/1998 | Truitt et al. | |
| 5,910,252 A | 6/1999 | Truitt et al. | |
| 5,919,369 A | 7/1999 | Ash | |
| 6,083,187 A * | 7/2000 | Nakayama et al. | 604/6.01 |
| 6,264,680 B1 | 7/2001 | Ash | |
| 6,348,162 B1 * | 2/2002 | Ash | 252/184 |
| 6,409,968 B1 * | 6/2002 | Takahashi | 422/64 |
| 6,471,872 B2 | 10/2002 | Kitaevich et al. | |
| 6,638,477 B1 * | 10/2003 | Treu et al. | 422/44 |
| 6,730,233 B2 | 5/2004 | Pedrazzi | |
| 6,793,643 B1 | 9/2004 | Briggs | |
| 7,351,218 B2 * | 4/2008 | Bene | 604/6.07 |
| 2003/0216660 A1 * | 11/2003 | Ben-Oren et al. | 600/532 |
| 2004/0089594 A1 * | 5/2004 | Collins et al. | 210/197 |
| 2004/0154967 A1 | 8/2004 | Pedrazzi | |
| 2005/0131331 A1 * | 6/2005 | Kelly et al. | 604/4.01 |
| 2005/0273016 A1 * | 12/2005 | Colman et al. | 600/529 |
| 2005/0277912 A1 * | 12/2005 | John | 604/890.1 |
| 2006/0213835 A1 * | 9/2006 | Nimura et al. | 210/645 |

\* cited by examiner

ON DEMAND AND POST-TREATMENT DELIVERY OF SALINE TO A DIALYSIS PATIENT

RELATED APPLICATIONS

This application claims priority to U.S. Provisional Application Ser. No. 60/756,772, filed Jan. 6, 2006, which is hereby incorporated by reference.

FIELD

This technology relates to the delivery of saline to a patient during both dialysis treatment and post-dialysis treatment.

BACKGROUND

The purpose of kidney dialysis is to remove waste materials from blood that are normally removed by properly functioning kidneys. During dialysis, blood and dialysate are passed through a dialyzer on opposite sides of a membrane within the dialyzer. The dialysis system is maintained under specific pressure and flow conditions such that blood waste compounds pass through the membrane from the blood side to the dialysate side where they can be safely removed. Water molecules also can pass through the membrane during dialysis. The removal of some water from the blood can be beneficial to patients under certain circumstances. In other circumstances, however, it is desirable to replace water lost across the membrane during dialysis.

SUMMARY

The claimed invention provides an apparatus for the delivery of saline into the extracorporeal blood flow path of a dialysis system. The apparatus includes a dialyzer, a blood inlet conduit connected to the dialyzer, and a blood flow regulator that controls fluid flow along the blood inlet conduit. A saline conduit connects a saline reservoir to the blood inlet conduit between the blood flow regulator and the dialyzer. A saline flow regulator controls fluid flow through the saline conduit. The apparatus further includes a controller that is operatively interconnected with the blood flow regulator and the saline flow regulator to automatically close the blood flow regulator and open the saline flow regulator in response to a signal calling for delivery of saline into the blood inlet conduit. The controller is further operative to automatically close the saline flow regulator and open the blood flow regulator, thereby halting saline delivery into the blood inlet conduit. Additionally, the controller can be configured to automatically deliver saline to the blood inlet conduit from the saline reservoir after a dialysis treatment has concluded, but before the patient is disconnected from the dialysis system in response to a signal calling for the delivery of saline into the blood inlet conduit.

The claimed invention further provides an apparatus for warning a patient that a dialysis treatment is about to end. The apparatus includes an alarm and a controller. The controller is operative to monitor the dialysis treatment and to activate the alarm at a predetermined time before the end of a dialysis treatment.

DETAILED DESCRIPTION

Figure 1:
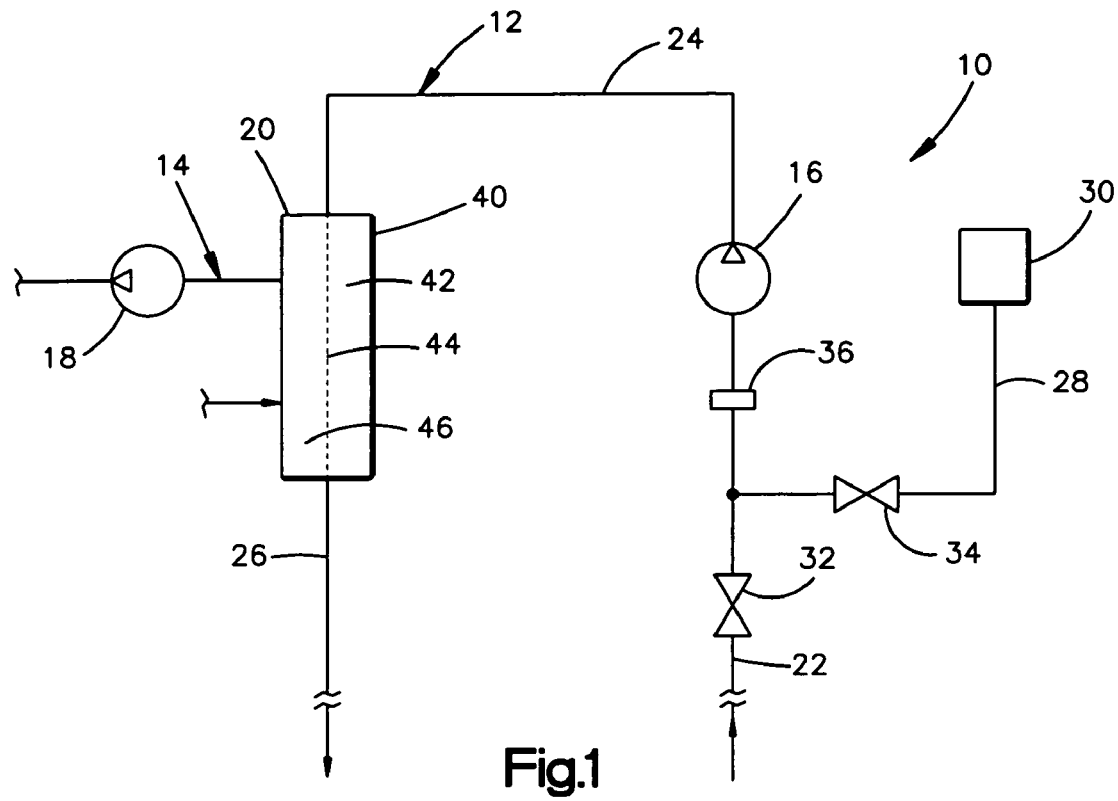
FIG. 1 is a schematic view of a dialysis system capable of providing saline on demand.

The dialysis systems shown schematically in the drawings can be operated in steps that are examples of the elements recited in the claims. The illustrated system thus includes examples of how a person of ordinary skill in the art can implement and use the claimed invention. Specifically, this description presents examples of methods for automatically delivering a bolus of saline to a patient upon the initiation of a signal from an operator, delivering saline to a patient after dialysis treatment has terminated, and providing a signal to a patient that treatment is about to end. This description is provided to meet the written description, best mode, and enablement requirements of the patent statute without imposing limitations that are not recited in the claims.

As shown in FIG. 1, an example of a dialysis system 10 includes a pair of distinct hydraulic systems 12 and 14. The first hydraulic system 12 provides an extracorporeal blood flow path that contains a patient's blood during dialysis. The second hydraulic system 14, which is shown partially, contains dialysate fluid. A first pump 16 drives blood through the blood system 12. A second pump 18 drives dialysate through the dialysate fluid system 14. The pumps 16 and 18 may comprise any suitable devices known in the art, although the first pump preferably comprises a body fluid pumping assembly as described in U.S. patent application Ser. No. 10/399,128, filed Jul. 28, 2003 (published as US2004/0050789), which is hereby incorporated by reference. The blood system 12 and dialysate fluid system 14 overlap at a dialyzer 20, but are otherwise separate from each other. Blood impurities and other blood components, including water molecules, pass from the blood and into the dialysate fluid as the blood and dialysate fluid both flow through the dialyzer 20.

The blood system 12 further includes a blood inlet conduit 22 into which blood flows from a patient. The blood inlet conduit 22 extends from the patient to the first pump 16. A blood transfer conduit 24 extends from the first pump 16 to the dialyzer 20. A blood outlet conduit 26 extends from the dialyzer 20 to return treated blood to the patient. The blood inlet conduit 22 and blood outlet conduit 26 are connected to the patient in such a manner that the patient's blood can flow into the blood inlet conduit 22 from the patient and back to the patient from the blood outlet conduit 26. In this arrangement, the blood inlet conduit 22, the blood transfer conduit 24, and the blood outlet conduit 26 complete a blood flow path along which a patient's blood can circulate through the blood system 12, as viewed in FIG. 1 under the influence of the first pump 16.

As further shown schematically in FIG. 1, a saline conduit 28 is hydraulically connected to the blood inlet line 22 upstream of the first pump 16. The saline conduit 28 communicates the blood inlet line 22 to a saline reservoir 30. A blood flow regulator 32 controls the flow of blood through the blood inlet conduit 22. A saline flow regulator 34 controls the flow of saline through the saline conduit 28. The regulators 32 and 34 could be simple clamps or on/off valves.

A fluid flow sensor 36 also is included in the blood system 12. The fluid flow sensor 36 is located downstream of the point at which the saline conduit 28 connects to the blood inlet line 22 and upstream of the first pump 16. The fluid flow sensor 36 may comprise any suitable device known in the art, but preferably is an ultrasonic flow sensor such as, for example, a Transonic Model H4E Flow Sensor (Transonic Systems Inc., Ithaca, N.Y.).

The dialyzer 20 is a known device including a housing 40 containing a semi-permeable membrane 44. The membrane 44 is disposed between the blood system 12 and the dialysate fluid system 14. In the configuration of the dialysis system 10 shown in FIG. 1, blood flows in one direction through housing 40 along the blood side 42 of the membrane 44, and dialysate fluid flows in the opposite direction through the housing 40 on the dialysate side 46 of the membrane 44. Blood waste compounds, such as urea, are small enough to pass through the membrane 44 from the blood side 42 to the dialysate side 46, but blood cells and other blood components are too large to pass through the membrane 44 and are thus retained in the blood. Other blood components, such as water molecules, also are small enough to pass through the membrane 44 from the blood side 42 to the dialysate side 46.

Several factors effect the transfer of blood impurities and other small molecule blood components from the blood side 42 to the dialysate side 46 of the membrane 44. One such factor is a pressure differential across the membrane 44. If the hydraulic fluid pressure is higher on one side of the membrane 44, fluid will flow across the membrane from the higher pressure side to the lower pressure side in order to equalize the pressure across the membrane 44. Fluid flow across the membrane 44 due to pressure differences is only size selective with respect to the components flowing across the membrane. Therefore, water molecules, minerals, and other small molecule blood components will flow across the membrane 44 under the influence of a pressure gradient. A pressure-driven flow across a membrane from the blood side to the dialysate side is known as ultrafiltration.

Figure 2:
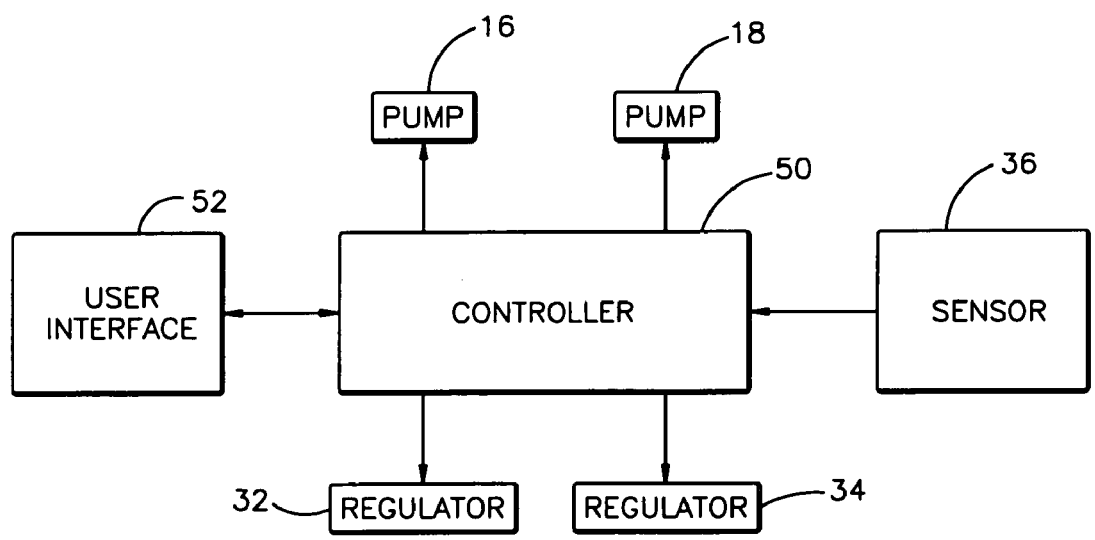
FIG. 2 is a schematic view showing parts of the system of FIG. 1.

As shown schematically in FIG. 2, the dialysis system 10 further includes a controller 50 and a user interface 52. The controller 50 is operatively interconnected with the pumps 16 and 18, the blood flow regulator 32, the saline flow regulator 34, the fluid flow sensor 36, and the user interface 52. The controller 50 has hardware and/or software configured for operation of these components 16, 18, 32, 34, 36, and 52, and may comprise any suitable programmable logic controller or other control device, or combination of control devices, that is programmed or otherwise configured to perform as recited in the claims. The user interface 52 provides means for an operator to receive information and provide input related to the operation of the dialysis system 10 by the controller 50.

The blood system 12 may also include, for example, various valves for starting and stopping fluid flow, fluid pumps or other fluid flow generating devices, flow meters for detecting flow and measuring flow rates, an ammonia and/or ammonium ion monitoring device to detect ammonia molecules and/or ammonium ions, air detectors for detecting air bubbles in the dialysis system, and other known devices that may take part in the performance of a dialysis treatment on a patient. Such other devices, which are well known to those skilled in the art, are omitted from the drawings for clarity of illustration.

In operation, when actuated by the operator the controller 50 initiates a dialysis treatment by starting pumps 16 and 18 to initiate flows of blood and dialysate through their respective systems 12 and 14. Unless saline is being delivered, the blood flow regulator 32 is open and the saline flow regulator 34 is closed. The dialyzer 20 then allows blood waste compounds to be transferred from the blood system 12 to the dialysate system 14. Under ultrafiltration conditions, water molecules and other small molecule blood components are also transferred from the blood system 12 to the dialysate system 14.

The controller 50 is operable in a different mode for saline bolus administration. For example, upon initiation of a signal from an operator through interaction with the user interface 52, the controller 50 can automatically deliver a bolus of saline from the saline reservoir 30 into the blood inlet line 22. The term "bolus" is used here to mean a predetermined volume of fluid provided to a patient in one dose. When such a saline bolus is to be administered, the blood flow regulator 32 is closed and the saline flow regulator 34 is opened. With this configuration of flow regulators, blood flow from the patient is halted and saline flows from the saline reservoir 30 toward and through the pump 16. When saline delivery is to be halted, the saline flow regulator 34 is closed and the blood flow regulator 32 is opened.

Initiation of a saline bolus administration event can occur at any time during a dialysis treatment. Saline bolus administration is initiated by either the operator or the patient through interaction of the operator or the patient with the user interface 52.

The volume of saline delivered during a given saline bolus administration can be controlled. Specifically, during a bolus administration the volume of saline delivered is monitored and delivery is stopped when the desired volume is reached. The volume of saline delivered in this manner can be measured by several methods. One method for measuring saline volume delivered during a bolus administration is for the controller 50 to monitor the rate of the pump 16 for the amount of time the saline flow regulator 34 is open. If the rate at which the pump 16 is pumping fluid and the amount of time the saline flow regulator 34 is open are known, the volume of saline added to the blood system can be calculated. Another method for measuring the volume of saline delivered during a bolus administration is for the controller 50 to monitor the fluid flow sensor 36. The fluid flow sensor 36 can monitor the volume of fluid flowing past its position during the period of time the saline flow regulator 34 is open.

The volume of saline delivered in a single bolus can be preset by a medical professional or can be set by the operator or patient at the time the bolus delivery is requested. For example, the saline bolus volume can be preset to about 100 mL, about 200 mL, or about 300 mL. Further, a preset array of saline bolus volumes could be available for the operator or patient to chose from such as, for example, the choice of about 100 mL, about 200 mL, or about 300 mL.

The total volume of saline available for delivery as well as the total volume of saline delivered to a patient can be monitored by the controller 50. The controller 50 can restrict bolus volume in order to reserve saline for other dialysis treatment tasks such as blood rinse-back at the end of treatment. At the end of a dialysis treatment it is desirable to return as much blood volume in the blood system 12 to the patient as possible. This is typically accomplished by rinsing the blood lines with saline and, in effect, pushing the blood in the blood system 12 back to the patient. Thus, a certain minimum volume of saline needs to be retained if this function is to be performed. Limiting the volume of saline available for saline boluses in this manner in a fixed, unreplenished volume system can act to limit the total volume of saline available for delivery to the patient via boluses. Additionally, the controller 50 can be configured to alert the operator or patient of a low saline volume condition. Then the saline volume could be replenished if additional saline volume is required or desired.

If sufficient saline volume remains or the saline volume has been replenished when a dialysis treatment is complete, a portion (or all) of the remaining or replenished saline can be delivered to the patient before the patient is disconnected. An operator or patient can initiate a post dialysis saline treatment through interaction with the user interface 52. Effecting post-treatment saline administration in the above described system involves closing the blood flow regulator 32 and opening the saline flow regulator 34. Halting post-treatment saline administration involves closing the saline flow regulator 34. The volume of saline delivered post-treatment can be monitored as discussed above. This post-treatment administration can occur in a set amount of time, for example, over the course of an hour or the delivery of a specific volume could be specified. The volume of saline that is delivered post-treatment and/or the post-treatment saline delivery time can be controlled by a medical professional.

The controller 50 is also operative to record the saline bolus and post treatment saline delivery practices of a patient. Information such as, for example, the total volume of saline delivered, individual saline bolus volume, the number of saline boluses requested, the time during treatment that saline boluses were requested, the volume of saline delivered during post-dialysis saline delivery, and the duration of post-dialysis saline delivery can be recorded. This information can then be made available to a medical professional for analysis.

The controller 50 is further operative to monitor a dialysis treatment and activate an alarm to alert the operator and/or patient that the dialysis treatment is close to completion. This alarm may provide an indication that blood rinse-back will occur. The alarm may be audible or visual or both and can be provided through the user interface 52. The alarm may indicate that the dialysis treatment is scheduled to end in a predetermined amount of time such as, for example, five minutes. The alarm can, for example, be a countdown clock that beeps at certain intervals, such as, for example, one minute intervals.

This written description sets forth the best mode of the invention, and describes the invention so as to enable a person skilled in the art to make and use the invention, by presenting examples of the elements recited in the claims. The patentable scope of the invention is defined by the claims, and may include other examples that occur to those skilled in the art. Such other examples, which may be available either before or after the application filing date, are intended to be within the scope of the claims if they have structural elements that do not differ from the literal language of the claims, or if they include equivalent structural elements with insubstantial differences from the literal language of the claims.

The invention claimed is:

1. An apparatus comprising:
   a dialyzer;
   a blood inlet conduit configured to convey blood from a patient to the dialyzer;
   a saline reservoir;
   a saline conduit connecting the saline reservoir to the blood inlet conduit;
   a saline flow regulator configured to control fluid flow through the saline conduit; and
   a controller configured to administer successive doses of saline to a patient connected to the blood inlet conduit by successively opening and closing the saline flow regulator to permit a dose volume of saline to flow into the blood inlet conduit;
   wherein the controller is further configured to operate the saline flow regulator in a blood rinse-back mode, and to retain a minimum volume of saline to perform blood rinse-back before the patient is disconnected by preventing a user from dispensing saline that would decrease the remaining volume below a reserve volume.

2. An apparatus as defined in claim 1 wherein the controller is configured to record the successive doses of saline to establish a medical record.

3. An apparatus as defined in claim 1 wherein the controller has a user interface configured for a user to choose from a preset array of dose volumes.

4. An apparatus as defined in claim 1 wherein the controller has a user interface configured for a user to input a signal calling for a dose of saline to a patient connected to the blood inlet conduit, and the controller is configured to administer a dose of saline in response to the signal any time during a dialysis treatment.

* * * * *